(12) United States Patent
Bologna et al.

(10) Patent No.: US 7,709,026 B2
(45) Date of Patent: May 4, 2010

(54) LOW CONCENTRATION OF PEROXIDE FOR TREATING OR PREVENTING VAGINAL INFECTIONS

(75) Inventors: William J. Bologna, Paris (FR); Howard L. Levine, Oceanside, NY (US)

(73) Assignee: Columbia Laboratories, Inc., Livingston, NJ (US)

( * ) Notice: Subject to any disclaimer, the term of this patent is extended or adjusted under 35 U.S.C. 154(b) by 230 days.

(21) Appl. No.: 10/278,910

(22) Filed: Oct. 24, 2002

(65) Prior Publication Data
US 2003/0091644 A1     May 15, 2003

Related U.S. Application Data

(60) Provisional application No. 60/330,683, filed on Oct. 29, 2001.

(51) Int. Cl.
*A61K 9/14*     (2006.01)
(52) U.S. Cl. .................................................. 424/486
(58) Field of Classification Search ................ 424/486, 424/428, 616, 469
See application file for complete search history.

(56) References Cited

U.S. PATENT DOCUMENTS

| | | | |
|---|---|---|---|
| 2,798,053 A | 7/1957 | Harold | |
| 2,923,692 A | 2/1960 | Ackermann | |
| 2,980,655 A | 4/1961 | Glass | |
| 4,127,515 A * | 11/1978 | MacRae et al. | 521/112 |
| 4,607,101 A * | 8/1986 | Bernstein | 514/24 |
| 4,615,697 A * | 10/1986 | Robinson | 424/428 |
| 4,657,935 A * | 4/1987 | Teplicki | 514/724 |
| 4,670,256 A | 6/1987 | Doran | 424/93 |
| 4,781,923 A * | 11/1988 | Pellico | 424/616 |
| 4,923,677 A | 5/1990 | Simon et al. | 422/37 |
| 4,997,625 A | 3/1991 | Simon et al. | 422/29 |
| 5,188,826 A * | 2/1993 | Chandrasekaran et al. | 424/78.04 |
| 5,330,761 A * | 7/1994 | Baichwal | 424/469 |
| 5,332,582 A * | 7/1994 | Babcock et al. | 424/78.04 |
| 5,340,836 A | 8/1994 | Reinhard et al. | 514/557 |
| 5,376,006 A | 12/1994 | Fischer | 433/215 |
| 5,466,463 A | 11/1995 | Ford | 424/433 |
| 5,472,704 A * | 12/1995 | Santus et al. | 424/435 |
| 5,536,743 A | 7/1996 | Borgman | 514/39.8 |
| 5,571,533 A * | 11/1996 | Santus et al. | 424/469 |
| 5,573,765 A | 11/1996 | Reinhard et al. | 424/93.45 |
| 5,667,817 A | 9/1997 | Kross | 424/661 |
| 5,741,525 A * | 4/1998 | Larsen | 424/616 |
| 5,778,886 A | 7/1998 | Shihata | 128/832 |
| 5,819,742 A | 10/1998 | Sokal et al. | 128/830 |
| 5,840,744 A | 11/1998 | Borgman | 514/398 |
| 5,843,998 A * | 12/1998 | Song et al. | 514/588 |
| 5,898,037 A | 4/1999 | Marx | 424/49 |
| 5,958,443 A | 9/1999 | Viegas et al. | 424/427 |
| 5,958,461 A | 9/1999 | Larsen | 424/614 |
| 6,017,521 A * | 1/2000 | Robinson et al. | 424/78.02 |
| 6,017,554 A | 1/2000 | Ratcliff | 424/422 |
| 6,093,394 A | 7/2000 | Chrisope | 424/93.45 |
| 6,117,859 A * | 9/2000 | Evans et al. | 514/166 |
| 6,125,850 A | 10/2000 | Sokal et al. | 128/830 |
| 6,159,491 A | 12/2000 | Durrani | 424/430 |
| 6,200,551 B1 | 3/2001 | Morgan | 424/53 |
| 6,235,314 B1 * | 5/2001 | Niazi | 424/486 |
| 6,277,363 B1 | 8/2001 | Ratcliff | 424/78.02 |
| 6,280,716 B1 | 8/2001 | Ratcliff | 424/78.02 |
| 6,303,147 B1 * | 10/2001 | Gilis | 424/484 |
| 6,407,288 B1 * | 6/2002 | Coburn et al. | 564/169 |
| 7,049,000 B2 * | 5/2006 | Fossum et al. | 428/402 |
| 2003/0211173 A1 | 11/2003 | Veach et al. | 424/670 |
| 2009/0156672 A1 * | 6/2009 | Budunova et al. | 514/546 |

FOREIGN PATENT DOCUMENTS

| | | |
|---|---|---|
| WO | 95/07699 | 3/1995 |
| WO | 96/10989 | 4/1996 |
| WO | 99/13862 | 3/1999 |
| WO | WO 99/65538 | 12/1999 |
| WO | 00/10536 | 3/2000 |
| WO | WO 01/28515 | 4/2001 |

OTHER PUBLICATIONS

Desesso et al. ("Assessment of the carcinogenicity associated with oral exposures to hydrogen peroxide," Food and Chemical Toxicology 38 (2000), pp. 1021-1041.*

Jian-Hwa Guo, (Excipient Update, "CARBOPOL Polymers for Pharmaceutical Drug Delivery Applications" in Drug Delivery Technology, 2001-2006, copyright).*

(Continued)

*Primary Examiner*—Blessing M Fubara
(74) *Attorney, Agent, or Firm*—Winston & Strawn LLP

(57) ABSTRACT

The invention relates to a pharmaceutical vaginal composition for treating or preventing vaginal infections. The composition includes a synergistic mix of a bioadhesive, extended release formulation that decreases the pH and that contains a peroxide in an amount sufficient to increase oxygen concentration without sterilizing the vagina or substantially killing the normally-desired local vaginal flora. The invention also relates to a method of treating or preventing vaginal infections in a patient comprising inserting vaginally an amount of the pharmaceutical vaginal composition in an amount sufficient to decrease the pH and increase oxygen concentration without sterilizing the vagina or substantially killing the normally-desired local vaginal flora.

33 Claims, No Drawings

OTHER PUBLICATIONS

Noveon Pharmaceutical Ingredients>Products Webpage; Noveon: The Specialty Chemicals Innovator™; http://www.pharma.noveon.com/products/default.asp; (2001-2006).

Noveon Pharmaceutical Ingredients>Products>CARBOPOL® Polymers Webpage; Noveon: The Specialty Chemicals Innovator™; http://www.pharma.noveon.com/products/Carbopol_detail.asp; (2001-2006).

Noveon Pharmaceutical Ingredients>Products>NOVEON® Polycarbophil Webpage; Noveon: The Specialty Chemicals Innovator™; http://www.pharma.noveon.com/products/polycarbophils_detail.asp; (2001-2006).

NOVEON® AA-1 Polycarbophil, USP Overview Sheet; Noveon: The Specialty Chemicals Innovator™; (Jul. 5, 2006).

CARBOPOL® 974P NF Polymer Overview Sheet; Noveon: The Specialty Chemicals Innovator™; (Jul. 5, 2006).

CARBOPOL® 934P NF Polymer Overview Sheet; Noveon: The Specialty Chemicals Innovator™; (Jul. 5, 2006).

USPTO Trademark Electronic Search System for CARBOPOL®; http://tess2.uspto.gov/bin/showfield?f=doc&state=h8af6s.2.2; (Oct. 28, 2006).

"Acne," Benign Diseases of the Vulva and Vagina, Kaufman, et al., 3$^{rd}$ Edition, 1989, pp. 288 and 289.

"Infection," Benign Diseases of the Vulva and Vagina, Kaufman, et al., 3$^{rd}$ Edition, 1989, pp. 1-15.

"Acne," Taber's Cyclopedic Medical Dictionary, 1997, pp. 31 and 32.

"Infection," Taber's Cyclopedic Medical Dictionary, 1997, pp. 1087-1091.

Label of CVS brand "Acne Treatment—benzoyl peroxide acne medication, vanishing formula," CVS Pharmacy, Inc., © 2005.

Label of CVS brand "Acne Treatment Gel—10% benzoyl peroxide acne medication," (maximum strength), CVS Pharmacy, Inc., © 2007.

Mashkovskii, M.D. Lekarstvennie sredstva. Posobie dlya vrachei. Tom 2, Moskva, Novaya volna, May 3, 2001. p. 376.

\* cited by examiner

LOW CONCENTRATION OF PEROXIDE FOR TREATING OR PREVENTING VAGINAL INFECTIONS

CROSS-REFERENCE TO RELATED APPLICATION

This application claims the benefit of U.S. Provisional Application No. 60/330,683, filed Oct. 29, 2001, the content of which is expressly incorporated herein by reference thereto.

FIELD OF THE INVENTION

This invention relates to a pharmaceutical composition for treating or preventing vaginal infections. The pharmaceutical composition generally comprises a synergistic mix of a bioadhesive, extended release formulation that releases and maintains a very low concentration of peroxide over an extended period of time to provide benefits of oxygen release, while decreasing pH decrease over time, but without excessive peroxide concentrations. The invention also relates to a method of treating vaginal infections using the pharmaceutical composition disclosed herein.

BACKGROUND OF THE INVENTION

Vaginal infections are a common problem among women. Bacterial Vaginosis (BV) is the most common form of infectious vaginitis, accounting for 45% of symptomatic cases and estimated to be present in 15% of asymptomatic sexually active women. See Breen, J. ed., *The Gynecologist and the Older Patient*, pp. 304-305 (1988). It is a polymicrobial vaginal infection believed to be caused by an increase in the number of anaerobic organisms with a concomitant decrease in lactobacilli in the vagina. The decrease in the number of lactobacilli in the vagina has a dual effect, i.e., (i) a decreased competition for nutrients, and (ii) a decrease in the amount of lactic acid present, thus allowing for the multiplication of opportunistic pathogens in the vagina, whose growth is normally suppressed by the lactobacilli. The principal pathogens associated with BV are believed to be Gardnerella vaginalis and anaerobes of the Mobiluncus species. However, numerous other pathogenic anaerobes are also believed to be involved in the etiology of vaginosis. See Kaufman et al., *Benign Diseases of the Vulva and Vagina*, 3rd ed., pp. 401-418 (1989). Thus, BV is considered a broad spectrum infection requiring a broad spectrum treatment.

In the United States discharge and foul smelling odor resulting from BV results in millions of women going to a physician's office each year in search of relief. An even larger number, estimated to be 30% of all adult American women, use douches that they purchase without a prescription. The idea of washing out the foul smelling discharge with an acid douche has a simplistic appeal. Medically, douching is frowned upon as studies have reported an association between douching and PID (Pelvic Inflammatory Disease), ectopic pregnancy, tubal infertility or reduced fertility. Furthermore, douching is unfavorable due to the fact that it also washes out normal and beneficial bacterial flora, leaving an environment prone to reoccurring BV.

The most troublesome aspect of BV is its impact upon the quality of fetal implantation and its potential to induce premature labor. The prevalence of BV in pregnant women has been reported to be 13 to 31%. BV during pregnancy is associated with increased risk of late miscarriage, pre-term labor, postpartum endometritis and low birth weight infants. In a recent study it was shown that BV is associated with an increased risk of miscarriage in the first trimester in women undergoing in-vitro fertilization.

U.S. application Ser. No. 09/748,753 discloses compositions useful in preventing miscarriage and premature labor associated with bacterial vaginosis by buffering the vaginal pH. The composition disclosed in the application comprises a therapeutically-effective amount of an aqueous pH-buffering bioadhesive water-insoluble, but water-swellable cross-linked polycarboxylic acid polymer, which provides the therapeutic effect without needing any additional treating agent, by itself buffering the vaginal pH to a normal, acidic pH, hostile to the infectant.

Clinically, BV presents itself as a superficial vaginal infection with few irritative symptoms and no inflammatory response. Some noticeable symptoms include an unpleasant smell, an elevated vaginal pH greater than about 5.0, a thin homogeneous discharge, the presence of Gardnerella clue cells and a high succinate/lactate ratio (not less than 0.4). See, e.g., Livengood et al., "*Bacterial Vaginosis: Diagnostic and Pathogenic findings during Topical Clindamycin Therapy*," Am. J. Obstet. Gynecol., Vol. 163, No. 2, p. 515 (August 1990).

It is believed that the composition of organic acids in the vagina shifts from primarily lactic acid ($pK_a$=3.86) to succinic acid ($pK_{a1}$=4.27, $pK_{a2}$=5.64) as a result of the decrease in lactobacilli, which produce lactic acid, and a rise in Mobiluncus, which produce succinic acid. This shift in acid composition tends to raise the vaginal pH. It is unclear whether the change in acidity is a cause or effect of the infection. However, it is known that certain undesirable anaerobes grow better at a higher pH than is normally present in the vagina. It is thus believed that lowering the vaginal pH to a normal healthy level is an effective measure against symptoms of the infection, if not the infection itself.

Moreover, the odor of the amines which are produced in the vagina during BV is known to increase at higher pH's because unprotonated, volatile amines are more prevalent at higher pH—as the environment becomes more basic. Additionally, the higher pH level is thought to allow the undesirable anaerobes to grow and produce the odor-causing amines that are associated with a bacterial vaginosis infection.

U.S. Pat. No. 6,017,521 (the "521 patent") discloses a method of treating BV by topically contacting the luminal surface of vaginal epithelial cells with an effective pH buffering amount of an aqueous composition comprising water and an effective amount of a water-swellable, but water-insoluble, cross-linked pH buffering bioadhesive polymer wherein at least 80% of the monomers comprising said polymer contain at least one carboxyl group. The composition is kept in contact with the vaginal cells for a time period sufficient to lower the pH of the vagina to an acidic pH. The composition taught by the '521 patent is free of any treating agents.

The exact role of $H_2O_2$-producing lactobacilli is at best unclear. This may be the result of several factors the most important of which is concentration. Being able to detect $H_2O_2$-producing lactobacilli does not mean they are present in sufficient concentration to oxygenize the vagina and make the environment hostile to anaerobes. The solution many investigators have proposed is to add $H_2O_2$-producing lactobacilli to the vagina in high concentration as a means of eliminating the infection. The technical difficulties involved in such a project have prevented any investigator from developing a truly viable therapy.

Other attempts have been made to put $H_2O_2$ into a vaginal acidifier. However, those attempts have failed for two reasons. First, $H_2O_2$ is unstable in a gel and cannot be stored commercially. Second, the $H_2O_2$ concentration, which tends to be released quickly all at once, causing a "burst effect," not only obliterates the anaerobes, but also sterilizes the vagina making women more susceptible to reoccurring vaginal infections.

Such a treatment is disclosed in U.S. Pat. No. 5,741,525, (the "'525 patent"). The '525 patent discloses methods for maintaining or enhancing the normal protective function of vaginal flora by administering a therapeutically effective amount of a composition that has hydrogen peroxide in an amount of about 0.1% to about 3.0%. The '525 patent teaches that peroxide "amounts below about 0.1% have been found to be unsuitable to have any meaningful inhibitory effect on a wide variety of microorganisms." (The '525 patent at column 5, lines 57-59). The concentrations of hydrogen peroxide taught by the '525 patent to be useful in treating BV, however, are often detrimental to the growth of beneficial bacterial and can cause severe vaginal irritation and even vaginal peroxide burns. Furthermore, the treatment simply supplies a sudden burst of peroxide, killing a substantial number of bacteria and leaving it to chance as to whether a beneficial bacterial flora will recolonize or there will be a reoccurrence of BV.

Thus, there exists a need for an effective pharmaceutical composition for treating vaginal infections such as BV that does not have a "burst effect" causing vaginal irritation and excessively inhibiting or destroying beneficial bacterial flora. Furthermore, there is a need for a pharmaceutical composition that treats BV without sterilizing or significantly killing the normally-desired local vaginal flora the vagina and leaving it susceptible to reoccurring BV. There is also a need for a pharmaceutical composition that is simple to use and still effectively achieves a balance between inhibiting undesirable microorganisms, while providing a favorable environment for desirable local flora. The present invention successfully addresses these needs as detailed below.

SUMMARY OF THE INVENTION

The invention relates to a pharmaceutical composition for treating or preventing vaginal infections. The pharmaceutical composition includes a synergistic mix of a peroxide source and a bioadhesive, extended release polymer formulation. In one embodiment of the invention, the synergistic mix is designed to release peroxide over a period of time, which is usually at least 12 hours and often more than 48 hours. In a further embodiment of the invention the synergistic mix releases peroxide in an amount less than 0.1% by weight per hour. In an additional embodiment of the invention the synergistic mix includes less than 0.1% by weight of peroxide. The peroxide released in each of these embodiments is in an amount sufficient to therapeutically increase oxygen concentration, while the extended release polymer reduces the pH, thereby sufficiently suppressing the growth of anaerobic organisms responsible for BV without also sterilizing the vagina or significantly killing the normally-desired local vaginal flora. So long as the anaerobic organisms are not permitted to dominate the environment, BV should be prevented or treated.

The bioadhesive, extended release polymer formulation preferably includes a bioadhesive, water-swellable, water-insoluble, cross-linked polycarboxylic polymer. A non-limiting example of such a polymer is polycarbophil.

In one preferred embodiment, the synergistic mix includes carbamide peroxide as the peroxide source mixed with polycarbophil as the polymer.

The invention further relates to a method of treating or preventing a vaginal infection. The composition is vaginally administering to a subject in need of such treatment a therapeutically effective amount of the pharmaceutical vaginal compositions taught herein, without substantially adversely affecting the normally-desired local flora.

DETAILED DESCRIPTION OF THE PREFERRED EMBODIMENTS

The present invention is based on the use of unexpectedly low concentrations of peroxide over an extended period of time to provide a beneficial effect by treating or preventing vaginal infections without the peroxide sterilizing the vagina, or significantly killing normally-desired local vaginal flora, or causing significant irritation of the sensitive tissues of the vagina.

The phrase "normally-desired local vaginal flora" means bacteria which normally reside in the vagina of a healthy female. Normal flora include, for example the lactic acid family of bacteria in human subjects, such as, Tissier's *bacillus*. Microbes which constitute normal flora are well known (e.g., see *Principles and Practice of Infectious Diseases*, 3rd Ed., 1990, G. Mandell et al., ed., Churchill Livingstone Inc. New York).

The phrase "significantly killing" as used herein means substantially sterilizing the vagina of beneficial bacteria normally found in a healthy vaginal environment, wherein there is not a sufficient number of normally-desired local vaginal flora present and necessary to recolonize the vagina safely upon completion of the treatment regime.

In addition, the term "vaginal infection" includes any type of microorganism infecting the vagina of a patient which is not a normally-desired local vaginal flora, such as a bacterial or yeast infection, but specifically includes BV.

The term "peroxide source" as used herein is a compound from which peroxide can be released. To illustrate the meaning of peroxide source in contrast to peroxide, the following example is provided. If 0.1% to 0.25% by weight carbamide peroxide (peroxide source) is used in a pharmaceutical vaginal composition, the amount of peroxide, upon discounting the carbamide portion, would be about 0.034 to 0.085% by weight peroxide.

The term "dose" or "dosage form" as used in the specification and claims means a physically discrete amount of the pharmaceutical composition suitable for use as dosages by human female subjects. Each dose contains a predetermined quantity of peroxide source calculated to produce the desired therapeutic effect in association with the required pharmaceutical vehicle. The quantity of composition of peroxide in a dose, of course may be varied to provide release of peroxide in various concentrations or various quantities over different periods of time.

One embodiment of the present invention is a pharmaceutical vaginal composition useful in treating vaginal infections, especially BV. The composition typically comprises a synergistic mix of a bioadhesive, extended release formulation that contains a peroxide. The peroxide is released in an amount sufficient to therapeutically increase oxygen concentration while the extended release polymer also decreases the pH, allowing effective treatment or prevention of BV without sterilizing the vagina or substantially killing the normally-desired local vaginal flora.

In a particular embodiment, the vaginal composition is designed to release peroxide over a period of at least 12 hours, preferably over a period of at least 24 hours and even more preferably at least 48 hours. Other formulations of the composition are designed to release the peroxide over a period of at least 72 hours and at least 96 hours. The greater the period of time covered by one dose the less frequent dosing would be needed if sequential doses are desired.

In a further non-limiting embodiment, the vaginal composition includes a synergistic mix that releases peroxide in an amount of less than 0.1% peroxide per hour. Preferably, the peroxide is released in an amount of less than 0.085% peroxide per hour. The compositions disclosed herein, which release low levels of peroxide, are surprisingly effective at treating and preventing vaginal infection without the negative effects of higher concentrations.

Some women lack a natural flora of peroxide-producing lactobacillus. In these women, the formulations disclosed herein are used to substitute for the function of these organisms, and to provide a more favorable environment for the other normally-desired local vaginal flora.

In an alternative embodiment of the invention, the pharmaceutical vaginal composition includes less than 0.1% peroxide in the composition to be administered to the patient. In this embodiment, the amount of peroxide being released over time is extremely low, while still being sufficient to treat or prevent vaginal infections.

The peroxide source may be selected from a variety of sources, both organic and inorganic. Typical forms of peroxide sources are those used for treating mucosa and related epithelial tissue, and particularly those used in dental bleaching application. Preferably the peroxide source is one of the following forms: hydrogen peroxide including its complexes (e.g., carbamide peroxide); alkyl peroxides (e.g., di t-butyl peroxide); benzyl peroxides (e.g., benzoyl peroxide); peroxyacids (e.g., m-chloroperbenzoic acid, peroxodisulfuric acid and its salts, peroxomonosulfuric acid and its salts); peroxyacid esters (e.g., t-butyl perbenzoate) dialkynitroxides (e.g., di t-butyl nitroxide).

Preferred peroxide sources include carbamide peroxide, alkyl peroxides, benzyl peroxides or dialkynitroxides. Most preferably, however, the peroxide source is carbamide peroxide.

The preferred bioadhesive polymeric system of the invention has the advantage of being capable of being held in the vagina, and providing extended release of peroxide, for relatively long periods of time, i.e., 48 to 72 hours or more and providing pH buffering in the normal physiologic range. In contrast, most drug delivery systems are sloughed off the vaginal walls in less than four hours. The polymer holds the peroxide source and slowly releases it over time. The preferred bioadhesive carrier includes a bioadhesive, water-swellable, water-insoluble, cross-linked polycarboxylic polymer. A particularly preferred bioadhesive, which may be in a gel formulation, contains a polycarbophil base designed to give controlled, extended release of peroxide over time.

The composition typically releases the peroxide over a period of at least 12 hours and preferably over a period of at least 24 hours. More preferably however the peroxide is released over a period of at least 48 hours and sometimes even more than 72 hours. Similar extended release formulations, albeit with other treating agents, are described in U.S. Pat. Nos. 5,543,150 and 6,126,959, the contents of which are each expressly incorporated herein by reference.

The specific peroxide delivery formulation chosen preferably includes a bioadhesive, water-insoluble, water-swellable, cross-linked polycarboxylic acid polymer formulation. An example of such a formulation in general is described in U.S. Pat. No. 4,615,697 (the "'697 patent"), the content of which is expressly incorporated herein by reference thereto. Typically, at least about 80% of the monomers of the polymer in such a formulation should contain at least one carboxyl functionality. The cross-linking agent should be present at such an amount as to provide enough bioadhesion to allow the system to remain attached to the target epithelial surfaces for a sufficient time to allow the desired dosing to take place.

For vaginal administration, the formulation preferably remains attached to the epithelial surfaces for a period of about 24 to 48 hours or more. Such results may be measured clinically over various periods of time, by testing samples from the vagina for pH reduction due to the continued presence of the polymer. This level of bioadhesion is generally attained when the cross-linking agent is present at about 0.1 to 6 weight percent of the polymer, preferably about 1 to 2 weight percent. Bioadhesion can also be measured using commercially available surface tensiometers utilized to measure adhesive strength.

The polymer formulation can be adjusted to control the release rate of the peroxide, by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene, and similar agents.

A preferred polymer for use in such a formulation is polycarbophil, U.S.P., which is commercially available from Noveon, Inc., of Cleveland, Ohio under the trade name NOVEON®-AA1. Polycarbophil is a polyacrylic acid cross-linked with divinyl glycol.

Other useful bioadhesive polymers that may be used in such a drug delivery system formulation are mentioned in the '697 patent. For example, these include polyacrylic acid polymers cross-linked with 3,4-dihydroxy-1,5-hexadiene, and polymethacrylic acid polymers cross-linked with divinyl benzene.

Typically, these polymers would not be used in their salt form, because this would significantly decrease their bioadhesive capability. Divalent salts, such as calcium salts, pose the greatest decrease in bioadhesion. Monovalent salts, such as sodium salts, do not tend to reduce bioadhesion as much.

Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

The bioadhesive formulation may be in the form of a gel, cream, tablet, pill, capsule, suppository, film, or any other pharmaceutically acceptable form that adheres to the mucosa and does not wash away easily. The preferred formulation for the present invention is in the form of a gel.

Additives such as those taught in the '697 patent may be mixed in with the cross-linked polymer in the formulation for maximum desired efficacy of the delivery system or for the comfort of the patient. Such additives, for example and without limitation, include lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

Advantageously, the peroxide may be delivered, and the vaginal pH can be reduced, for an extended period of time by utilizing the bioadhesive polycarbophil. Polycarbophil is a polymer lightly cross-linked with divinyl glycol. Polycarbophil is also a weak poly-acid containing multiple carboxyl radicals, which are the source of its negative charges. These acid radicals permit hydrogen bonding with the cell surface. Hydrogen bonds are weak, but in the case of polycarbophil they are numerous and therefore, tenacious. Polycarbophil is a water insoluble polymer and stays attached to the vaginal epithelial cells until they turnover, normally up to 3 to 5 days. Since polycarbophil is a weak poly-acid with an exceedingly high buffering capacity, it maintains the vaginal pH in the physiologic range, under 5, and thus, helps protect against infection. The effect has been shown to persist for more than 96 hours. Polycarbophil has a pKa of 4.3 and as with all good buffers it will adjust the environment close to its pKa.

The polymer described in the '697 patent may be adjusted to control the release rate of the peroxide, e.g., by varying the amount of cross-linking agent. Generally, the release rate of the peroxide source in the formulation is continuously about zero order release, relative to the amount of peroxide source present, after a small burst of release initially. Accordingly, the composition would readily be formulated by one of skill in the art so that the duration and release rate are adjusted to deliver an appropriate amount of peroxide. A typical composition of the polymer stays in place typically for about 48 hours.

A nonlimiting example of a suitable formulation for vaginal delivery of peroxide comprises polycarbophil, carbomer, Natrosol® 250 HHX, glycerol, sorbic acid, methyl hydroxybenzoate, and purified water mixed with a peroxide source, preferably carbamide peroxide or benzoyl peroxide.

Sorbic acid and methyl hydroxybenzoate are preservatives, which may be substituted by other known preservatives, such as benzoic acid, propylparaben, or propionic acid.

Carbomer is a gel former, preferably Carbopol 974P, but may be substituted by other gel formers including, but not limited to Carbopol 934P, Carbopol 980, methyl cellulose or propyl cellulose.

Natrosol® 250 HHX is a viscosity enhancing agent, which may be substitued by other known viscosity enhancing agents, such as methyl cellulose or propyl cellulose. Natrosol® 250 HHX is commercially available from Hercules, Inc., located in Wilmington, Del.

Glycerol is a humectant; alternative humectants include, for example, propylene glycol and dipropylene glycol.

As will be apparent to those skilled in the art, the composition can be varied to affect certain properties. For example, the concentration of the bioadhesive polymer can be adjusted to provide greater or lesser bioadhesion. The viscosity can be varied by varying the pH or by changing the concentration of the polymer or gel former. The pH also can be varied as appropriate to affect the release rate or bioadhesiveness of the formulation. All ingredients are well known and readily available from supplier known in the industry.

In a preferred embodiment, the invention includes a vaginal composition which includes a polycarbophil and carbamide peroxide in a synergistic mix formulated to release peroxide over at least 24 hours.

Preferred percentage of peroxide source included in the pharmaceutical composition is typically between 0.01% and 15%, but more preferable between 0.1% and 10% and most preferably between 0.25% and 7%.

Generally, the peroxide source present in a dosage amount of pharmaceutical vaginal composition, wherein the dosage amount is between 0.5 g and 2.5 g, and the peroxide source is in an amount of about 0.01 mg and 500 mg. In another example, the composition is formulated to be administered in an amount of about 1 g to about 2.5 g per dose and the peroxide amount in the composition is about 0.01 mg to about 100 mg. It is preferred, however, if the peroxide source is present in the composition in an amount of between about 0.1 mg to 75 mg and more preferably in amount of 1 mg to 50 mg.

The amount of peroxide in the formulation is typically between 0.0035 mg to 350 mg. Preferably, however, the formulations usually contain between 0.01 mg to 100 mg and more preferably between 0.1 mg and 75 mg peroxide.

The present invention further relates to a method of treating or preventing a vaginal infection in a subject. The method involves inserting vaginally a synergistic mix of a bioadhesive, extended release formulation that releases and maintains a low concentration of peroxide.

The method can be used to maintain normal vaginal floral activity. For example, if a patient is pregnant, and especially if they are susceptible to miscarriage, the dosage amount of the pharmaceutical compositions described herein may be administered to the patient to treat or prevent BV. As discussed above, BV during pregnancy has an impact upon the quality of fetal implantation and its potential to induce premature labor. The present invention is useful in preventing or treating BV in pregnant women or women attempting to become pregnant, and therefore reducing the risk of miscarriage and low birth weights of infants.

The compositions described herein may be administered to a patient by introducing it into the vaginal cavity by use of conventional applicators as known in the art, such as (without limitation) plunger, douche, and manually. One method of delivery is to use a device similar to those described in U.S. Design Pat. Nos. D345,211 and D375,352. These devices are oblong hollow tube containers, with one end capable of being opened and the other end containing most of the composition to be delivered in a sealed container that may be used relatively easily by the patient. The containers also maintain the formulation and treating agent in a sealed, sterile environment until used. Upon use, such a container is opened and the open end is inserted into the vagina, while the other end is squeezed to deliver the contents of the container into the vagina. such as tampon injectables or other coating or impregnating means. A 'kit' of the product can therefore contain a single dose or multiple doses of the product.

The quantity of pharmaceutical vaginal composition contained in a dose is generally at least about 0.5 g, and is not more than about 3 g. A typical and presently preferred dose is in a gel vehicle in the range of about 0.75 g to about 2 g and most preferably about 1 g to 1.5 g per dose. For example, composition is formulated to be administered in an amount of about 1 g to about 2 g per dose.

Advantageously, the dose may be formulated so that it may be taken as often as twice or more a day, or as infrequently as once or less per week. Preferably the dose is formulated so that the dose is taken only once a day and more preferably biweekly or even weekly.

EXAMPLES

The following examples are illustrative of preferred formulations of the invention. All percentages are based on the percent by weight of the formulation prepared unless otherwise indicated and all totals equal 100% by weight. The peroxide sources used for illustrative purposes in these examples were carbamide peroxide and benzoyl peroxide, but as explained above, several different peroxide sources can be used.

| CARBAMIDE PEROXIDE ALTERNATE FORMULATIONS | | | | | |
|---|---|---|---|---|---|
| Carbamide Peroxide | 0.10% | 0.10% | 0.25% | 1.00% | 0.25% |
| Polycarbophil USP | 2.00% | 2.00% | 2.00% | 2.00% | 1.00% |
| Carbopol 974P | 1.00% | 1.00% | 1.00% | 1.00% | — |
| Natrosol ®250 HHX | — | — | — | — | 2.00% |
| Glycerol USP/BP | 12.90% | 15.00% | 12.90% | 12.90% | 12.90% |
| Sorbic acid NF/EP | 0.08% | 0.80% | 0.08% | 0.08% | 0.08% |
| Methyl Hydroxybenzoate NF, EP | 0.18% | 0.18% | 0.18% | 0.18% | 0.18% |
| Purified water USP/EP | 83.74% | 80.92% | 83.59% | 82.84% | 83.59% |
| Total | 100% | 100% | 100% | 100% | 100% |

| CARBAMIDE PEROXIDE ALTERNATE FORMULATIONS | | | | | |
|---|---|---|---|---|---|
| Carbamide Peroxide | 0.25% | 5.00% | 5.00% | 10.00% | 14.00% |
| Polycarbophil USP | 1.00% | 2.00% | 1.00% | 2.00% | 2.00% |
| Carbopol 974P | — | 1.00% | — | 1.00% | 1.00% |
| Natrosol ® 250 HHX | 2.00% | — | 2.00% | — | — |
| Glycerol USP/BP | 14.00% | 12.90% | 12.90% | 12.90% | 12.90% |
| Sorbic acid NF/EP | 0.08% | 0.08% | 0.08% | 0.08% | 0.08% |
| Methyl Hydroxybenzoate NF, EP | 0.18% | 0.18% | 0.18% | 0.18% | 0.18% |
| Purified water USP/EP | 82.49% | 78.84% | 78.84% | 73.84% | 69.84% |
| Total | 100% | 100% | 100% | 100% | 100% |

| BENZOYL PEROXIDE ALTERNATE FORMULATIONS | | | | | |
|---|---|---|---|---|---|
| Benzoyl Peroxide | 0.20% | 0.20% | 0.50% | 0.50% | 0.50% |
| Polycarbophil USP | 2.00% | 2.00% | 2.00% | 1.00% | 1.00% |
| Carbopol 974P | 1.00% | 1.00% | 1.00% | — | — |
| Natrosol ® 250 HHX | — | — | — | 2.00% | 2.00% |
| Glycerol USP/BP | 12.90% | 15.00% | 12.90% | 12.90% | 14.00% |
| Sorbic acid NF/EP | 0.08% | 0.80% | 0.08% | 0.08% | 0.08% |
| Methyl Hydroxybenzoate NF, EP | 0.18% | 0.18% | 0.18% | 0.18% | 0.18% |
| Purified water USP/EP | 83.64% | 80.82% | 83.34% | 83.34% | 82.24% |
| Total | 100% | 100% | 100% | 100% | 100% |

| BENZOYL PEROXIDE ALTERNATE FORMULATIONS | | | | | |
|---|---|---|---|---|---|
| Benzoyl Peroxide | 1.00% | 5.00% | 5.00% | 10.00% | 14.00% |
| Polycarbophil USP | 2.00% | 2.00% | 1.00% | 2.00% | 2.00% |
| Carbopol 974P | 1.00% | 1.00% | — | 1.00% | 1.00% |
| Natrosol ® 250 HHX | — | — | 2.00% | — | — |
| Glycerol USP/BP | 12.90% | 12.90% | 12.90% | 12.90% | 12.90% |
| Sorbic acid NF/EP | 0.08% | 0.08% | 0.08% | 0.08% | 0.08% |
| Methyl Hydroxybenzoate NP, EP | 0.18% | 0.18% | 0.18% | 0.18% | 0.18% |
| Purified water USP/EP | 82.84% | 78.84% | 78.84% | 73.84% | 69.84% |
| Total | 100% | 100% | 100% | 100% | 100% |

The above formulations can be adjusted to maximize the particular delivery system used. For example, note the formulation with 14% carbamide peroxide would typically be used with a dosage regime that requires less frequent administration of the composition. With a composition having a high concentration of peroxide, a low concentration of peroxide could be released over longer duration, minimizing the number of dose administrations needed daily or weekly.

Any and all publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method of treating a bacterial or yeast infection of a vagina comprising vaginally administering to a subject in need of such treatment a therapeutically effective amount of a vaginal composition comprising an extended release formulation that includes a synergistic mix of a peroxide source and a bioadhesive, water-swellable, water-insoluble, cross-linked polycarboxylic polymer, with the composition releasing peroxide in an amount of less than 0.1% by weight per hour over a period of from at least 12 hours to about 96 hours to provide an increased oxygen concentration to therapeutically decrease pH without sterilizing the vagina or significantly killing the normally-desired local vaginal flora.

2. The method of claim 1, wherein the synergistic mix releases peroxide over a period of at least 24 hours.

3. The method of claim 2, wherein the peroxide source is present in an amount of about 0.01 mg to about 500 mg.

4. The method of claim 3, wherein the peroxide source is present in an amount of about 0.1 mg to about 75 mg.

5. The method of claim 2, wherein the peroxide source is carbamide peroxide.

6. The method of claim 5, wherein the carbamide peroxide is present in an amount of about 0.01% to about 15% by weight of the composition.

7. The method of claim 6, wherein the polymer is polycarbophil.

8. The method of claim 7, wherein the carbamide peroxide is in an amount of about 0.1% to about 0.25% by weight of the composition.

9. The method of claim 8, in single dosage form, wherein the composition is formulated to be administered in an amount of about 1 g to about 2 g per dose.

10. The method of claim 9, wherein the bacterial or yeast infection is bacterial vaginosis.

11. The method of claim 2, wherein the synergistic mix releases peroxide over a period of at least 48 hours.

12. The method of claim 2, wherein the peroxide amount in the composition is between 0.0035 mg to 350 mg.

13. The method of claim 12, wherein the peroxide amount is between 0.01 mg to 100 mg.

14. The method of claim 1, wherein the polymer is polycarbophil.

15. The method of claim 1, wherein the synergistic mix releases peroxide over a period of at least 72 hours.

16. The method of claim 1, wherein the bacterial or yeast infection is bacterial vaginosis.

17. A method of treating a bacterial or yeast infection of a vagina comprising vaginally administering to a subject in need of such treatment a therapeutically effective amount of a vaginal composition comprising an extended release formulation that includes a synergistic mix of a peroxide source and a bioadhesive, water-swellable, water-insoluble, cross-linked polycarboxylic polymer, with the composition releasing peroxide in an amount of less than 0.1% by weight per hour, wherein the released amount of peroxide therapeutically decreases pH and increases oxygen concentration without sterilizing the vagina or substantially killing the normally-desired local vaginal flora.

18. The method of claim 17, wherein the peroxide is present in an amount of about 0.1 to about 75 mg.

19. The method of claim 18, wherein the polymer is polycarbophil.

20. The method of claim 19, wherein the peroxide source is carbamide peroxide that includes an amount of peroxide of less than 0.1% by weight of the composition.

21. The method of claim 20, wherein the amount of peroxide, upon discounting the carbamide portion, is about 0.034% to about 0.085% by weight peroxide of the composition.

22. The method of claim 19, in dosage form, wherein the composition is formulated to be administered in an amount of about 1 g to about 2.5 g per single dosage.

23. The method of claim 19, wherein the peroxide amount in the formulation is 0.01 mg to 100 mg.

24. The method of claim 17, wherein the polymer is polycarbophil.

25. The method of claim 24, wherein the peroxide source is present in an amount of about 0.01 mg to about 500 mg.

26. The method of claim 25, wherein the peroxide source is present in an amount of about 0.1 mg to about 75 mg.

27. The method of claim 26, in single dosage form, wherein the composition is formulated to be administered in an amount of about 1 g to about 2.5 g per dose and the peroxide amount in the composition is about 0.01 mg to about 100 mg.

28. The method of claim 27, wherein the bacterial or yeast infection is bacterial vaginosis.

29. The method of claim 24, wherein the synergistic mix releases peroxide over a period from at least 24 hours to about 96 hours.

30. The method of claim 24, wherein the synergistic mix releases peroxide over a period from at least 48 hours to about 96 hours.

31. The method of claim 17, wherein the peroxide source is carbamide peroxide.

32. The method of claim 31, wherein the carbamide peroxide is present in an amount of about 0.01% to about 15% by weight of the composition.

33. The method of claim 17, wherein the bacterial or yeast infection is bacterial vaginosis.

\* \* \* \* \*

UNITED STATES PATENT AND TRADEMARK OFFICE
CERTIFICATE OF CORRECTION

PATENT NO.        : 7,709,026 B2
APPLICATION NO.   : 10/278910
DATED             : May 4, 2010
INVENTOR(S)       : Bologna et al.

Page 1 of 1

It is certified that error appears in the above-identified patent and that said Letters Patent is hereby corrected as shown below:

Title Page:
Item (56) References Cited, U.S. PATENT DOCUMENTS, add the following reference:
-- 5,667,492 A    9/1997   Bologna et al. .......... 604/57 --.

Column 3:
Line 20, change "bums." to -- burns. --.

Column 9:
Line 45, in the fourth formulation under the heading "BENZOYL PEROXIDE ALTERNATE FORMULATIONS", before "EP" change "NP," to -- NF, --.

Signed and Sealed this
Eighth Day of May, 2012

David J. Kappos
*Director of the United States Patent and Trademark Office*